United States Patent [19]

Yamamoto et al.

[11] Patent Number: 4,973,706
[45] Date of Patent: Nov. 27, 1990

[54] PROCESS FOR THE PREPARATION OF INDIGO COMPOUNDS

[75] Inventors: Yoshihiro Yamamoto, Yokohama; Usaji Takaki, Fujisawa; Shinobu Aoki; Isao Hara, both of Yokohama, all of Japan

[73] Assignee: Mitsui Toatsu Chemicals, Incorporated, Tokyo, Japan

[21] Appl. No.: 343,459

[22] Filed: Apr. 25, 1989

[30] Foreign Application Priority Data

Apr. 25, 1988 [JP] Japan ................. 63-100214

[51] Int. Cl.$^5$ ............................................. C09B 7/00
[52] U.S. Cl. ................................................... 548/457
[58] Field of Search ........................................ 548/457

[56] References Cited

U.S. PATENT DOCUMENTS 4,151,170 4/1979 Gosteli ................. 548/457

FOREIGN PATENT DOCUMENTS 0124027 9/1979 Japan ................. 548/457

54-124027 9/1979 Japan .

OTHER PUBLICATIONS

Beilsteins Handbuch der Organischen Chemie, Sachregister für die Bände 23-25.
Rodd's Chemistry of Carbon Compounds, vol. IV, Part B, Elsevier Scientific Publishing Company, 1977, pp. 350-357.

*Primary Examiner*—David B. Springer
*Attorney, Agent, or Firm*—Millen, White & Zelano

[57] ABSTRACT

Disclosed is a process for preparing an indigo compound in improved yield by reacting indole or other indole compound having no substituent at the 2- and 3-positions with an organic hydroperoxide in the presence of an additive selected from the group consisting of (1) a carboxyl compound and (2) a boric acid ester compound. The yield of the indigo compound can further be increased by using a metallic compound catalyst capable of oxidizing carbon atom at the 3-position of the indole compound, such as a compound of a metal of group 4A, 5A or 6A of the periodic table.

26 Claims, No Drawings

PROCESS FOR THE PREPARATION OF INDIGO COMPOUNDS

BACKGROUND OF THE INVENTION

1. Field of the Invention:

This invention relates to a process for the preparation of an indigo compound. More specifically, it relates to a process for the preparation of an indigo compound by reacting an indole compound having no substituent at the 2- and 3-positions with an organic hydroperoxide in the presence of a specific additive.

2. Description of the Related Art:

Indigo compounds are important compounds that are useful as dyes. The presently employed industrial processes for the preparation of indigo comprise forming an N-phenylglycine salt from aniline and chloroacetic acid, or from aniline, cyanic acid and formaldehyde, converting this salt into an indoxyl compound by alkali fusion at elevated temperature, and then oxidizing this compound with air. However, these processes are not only complicated ones involving many steps, but also require the use of large amounts of potassium hydroxide and sodium hydroxide. Moreover the recovery and reuse of used potassium hydroxide and sodium hydroxide has the disadvantage of consuming much energy and requiring special equipment. Therefore, conversion to a simpler process has been desired.

Meanwhile, it has been reported in the field of synthetic organic chemistry that a slight amount of indigo was formed by oxidation of indole. Specifically, Obata et al. have reported that, when peracetic acid, which is a percarboxylic acid, was produced from hydrogen peroxide and acetic acid in the reaction system and reacted with indole, a trimer of indole, or 2,2-diindyl ψ-indoxyl, was obtained and in addition a small amount of indigo was formed as a by-product (Bull. Agr. Chem. Soc. Japan, Vol. 20, pp. 80-83, 1956). Moreover, B. Witkop et al. have reported that, when perbenzoic acid, which is a percarboxylic acid, was reacted with indole in chloroform by allowing the reaction mixture to stand in a refrigerator overnight, a very small amount of indigo was formed together with a variety of other products (Justus Liebigs Annalen der Chemie, Vol. 558, pp. 91-98, 1947). Furthermore, A. K. Sheinkman et al. have reported that, when hydrogen peroxide, which is an inorganic peroxide, was reacted with indole in methanol, the trimer 2,2-diindyl-ψ-indoxyl was obtained in high yield, as was the case with the reaction using peracetic acid, and the formation of indigo was only detected by chromatography (Khim. Geterotsikl. Soedin., Vol. 11, pp. 1490-1496, 1978). However, all of these reports were concerned with a brief investigation on the reactivity of indole, and indigo that is the desired product in the present invention was nothing but a by-product formed in very small amounts. Accordingly, these are not satisfactory processes for the preparation of indigo compounds.

SUMMARY OF THE INVENTION

It is an object of the present invention to provide an improved and simple process for the preparation of indigo compounds.

It is another object of the present invention to provide a process for the preparation of indigo compounds which uses an indole compound as a starting material and can achieve higher efficiency than the above-described prior art processes.

The present inventors have carried on an exhaustive investigation on a wide variety of oxidizing agents and additives, with a view to developing a reaction system which can produce an indigo compound efficiently and simply by using, as a starting material, an indole compound which can readily be obtained industrially. As a result, it has now been found that, if an organic hydroperoxide, the usefulness of which has been unknown in the prior art, is used as an oxidizing agent and reacted with an indole compound in the presence of a specific additive, an indigo compound can readily be obtained in a single step while achieving a higher yield and formation rate than achievable in the above-described prior art processes using other oxidizing agents or than achievable in the case without using any additive. The present invention has been completed on the basis of these findings.

According to the present invention, there is provided a process for the preparation of an indigo compound which comprises reacting a corresponding indole compound having no substituent at the 2- and 3-positions with an organic hydroperoxide in the presence of an additive selected from the group consisting of (1) a carboxyl compound and (2) a boric acid ester compound.

DESCRIPTION OF THE PREFERRED EMBODIMENTS

The indole compound having no substituent at the 2- and 3-positions, which is used as one of the starting materials in the process of the present invention, is selected from the group consisting of indole; alkylindoles having 1 to 4 alkyl groups of 1 to 10 carbon atoms, such as 1-methylindole, 4-ethylindole, 5-methylindole, 6-methylindole, 6-isopropylindole, 7-methylindole and 4,5-dimethylindole; cycloalkylindoles having 1 to 4 cycloalkyl groups of 3 to 12 carbon atoms, such as 4-cyclohexylindole and 5-cyclopentylindole; arylindoles having 1 to 4 unsubstituted or alkyl-substituted aryl groups of 6 to 30 carbon atoms, such as 5-phenylindole and 6-β-naphthylindole; halogenated indoles having 1 to 4 halogen atoms, such as 4-chloroindole, 5-chloroindole, 5,7-dichloroindole, 5-bromoindole, 6-bromoindole, 5,7-dibromoindole and 4-chloro-5-bromoindole; hydroxyindoles having 1 to 4 hydroxyl groups, such as 4-hydroxyindole, 5-hydroxyindole and 4,5-dihydroxyindole; alkoxyindoles having 1 to 4 alkoxy groups of 1 to 10 carbon atoms, such as 4-methoxyindole and 5-benzyloxyindole; phenoxyindoles having 1 to 4 phenoxy groups of 6 to 30 carbon atoms, such as 5-phenoxyindole; halogenated alkylindoles having 1 to 3 halogen atoms and 1 to 3 alkyl groups of 1 to 10 carbon atoms, such as 4-chloro-5-ethylindole, 6-chloro-4-methylindole, 4-bromo-5-ethylindole and 5-bromo-4-methylindole; nitroindoles having 1 to 4 nitro groups, such as 4-nitroindole, 5-nitroindole and 7-nitroindole; acylindoles having 1 to 4 acyl groups of 2 to 20 carbon atoms, such as 1-benzoylindole and 4-acetylindole; acyloxyindoles having 1 to 4 acyloxy groups of 2 to 20 carbon atoms, such as 1-acetoxyindole and 4-benzoyloxyindole; indolecarboxylic acids, such as indole-5-carboxylic acid, and esters thereof; N,N-dialkylaminoindoles having 1 to 4 N,N-dialkylamino groups in which each alkyl group contains 1 to 10 carbon atoms, such as 5-N,N-dimethylaminoindole; and sulfonated indoles. Of course, these indole compounds should not have the above-described substituent groups at the 2- and 3-positions. In addition, indole compounds having a combination of two or more types of substituent groups as described above are also useful in the process of the present invention. At positions other than the 2- and 3-positions, these indole compounds may have any substituent that does not interfere with the reaction. Among these indole compounds, indole is especially preferred.

The organic hydroperoxide, which is used as the other starting material in the process of the present invention, is an organic compound having at least one hydroperoxy (—OOH) group. Useful organic hydroperoxides are listed, for example, in the tables given in D. Swern, "Organic Peroxides, Vol. II", Wiley-Interscience (1971), pp. 107–127 and in the tables given in A. G. Davies, "Organic Peroxides", Butterworths (1961), pp. 9–33. Among these organic hydroperoxides, secondary and tertiary alkyl hydroperoxides having 3 to 30 carbon atoms in the alkyl moiety, such as tert-butyl hydroperoxide, 1-phenylethyl hydroperoxide, 1-methyl-1-phenylethyl hydroperoxide (cumene hydroperoxide), bis(1-methylethyl)phenyl hydroperoxides, 1-methyl-1-(4-methylcyclohexyl)ethyl hydroperoxide, 2,5-dimethylhexane-2,5-dihydroperoxide and 1,1,3,3-tetramethylbutyl hydroperoxide, are preferred.

Among these compounds, tert-butyl hydroperoxide, 1-phenylethyl hydroperoxide and 1-methyl-1-phenylethyl hydroperoxide are especially preferred.

These organic hydroperoxides may be used alone, or two or more of them may be used in admixture or in sequence. Alternatively, it is also possible to use a suitable combination of components (e.g., isopropylbenzene and an oxygen-containing gas) which can produce such an organic hydroperoxide in the reaction system. Although the amount of organic hydroperoxide used is not critical, it is usually in the range of about 0.01 to about 100 moles, preferably about 0.1 to about 20 moles, per mole of the indole compound.

The additive used in the process of the present invention is selected from the group consisting of (1) a carboxy compound and (2) a boric acid ester compound.

The carboxyl compound used as the additive is a compound selected from the group consisting of carboxylic acids and carboxylic acid anhydrides. Examples of useful carboxylic acids include saturated aliphatic carboxylic acids such as formic acid, acetic acid, propionic acid, butyric acid, isobutyric acid, valeric acid, isovaleric acid, pivalic acid, caproic acid, caprylic acid, lauric acid, stearic acid, phenylacetic acid, diphenylacetic acid, 3-phenylpropionic acid, succinic acid, adipic acid and sebacic acid; unsaturated aliphatic carboxylic acids such as oleic acid, linoleic acid, linolenic acid, acrylic acid, methacrylic acid, cinnamic acid and fumaric acid; alicyclic carboxylic acids such as cyclohexanecarboxylic acid and cyclohexane-1,4-dicarboxylic acid; aromatic carboxylic acids such as benzoic acid, phthalic acid, isophthalic acid, terephthalic acid, trimesic acid, α-naphthalenecarboxylic acid and naphthalene-1,8-dicarboxylic acid; alkyl-substituted aromatic carboxylic acids such as p-methylbenzoic acid, m-isopropylbenzoic acid and toluene-3,5-dicarboxylic acid; halogen-substituted aromatic carboxylic acids such as o-chlorobenzoic acid, m-chlorobenzoic acid, p-chlorobenzoic acid, m-bromobenzoic acid, 2,4-dichlorobenzoic acid and 6-bromonaphthalene-1-carboxylic acid; hydroxy-substituted aromatic carboxylic acids such as m-hydroxybenzoic acid, p-hydroxybenzoic acid and 6-hydroxynaphthalene-1-carboxylic acid; alkoxy-substituted aromatic carboxylic acids such as o-methoxybenzoic acid, m-methoxybenzoic acid, p-ethoxybenzoic acid, 5-methoxynaphthalene-2-carboxylic acid and ethoxyterephthalic acid; and heterocyclic aromatic carboxylic acids such as nicotinic acid, isonicotinic acid and quinoline-3-carboxylic acid. These compounds may additionally have any substituent group that does not interfere with the reaction. Examples of useful carboxylic acid anhydrides include the anhydrides of the above-described carboxylic acids. Moreover, it is also possible to use a suitable compound, or combination of compounds, which can produce such a carboxyl compound in the reaction system.

The boric acid ester compound used as the additive is a compound selected from the group consisting of orthoboric acid esters and metaboric acid esters. Examples of useful orthoboric acid esters include trialkyl borates such as trimethyl borate, triethyl borate, triisopropyl borate, tri-sec-butyl borate, tri-tert-butyl borate, tricyclohexyl borate, trimenthyl borate and tribenzyl borate; triaryl borates such as triphenyl borate; and other boric acid esters such as menthoxyboric acid, 2-acetylacetonato-1,3,2-benzodioxaborole and 2-hexafluoroacetylacetonato-1,3,2-benzodioxaborole. Examples of useful metaboric acid esters include alkyl metaborates such as isopropyl metaborate, n-butyl metaborate, sec-butyl metaborate, tert-butyl metaborate, cyclohexyl metaborate and menthyl metaborate; and aryl metaborates such as phenyl metaborate and (2,6-di-tert-butyl-4-methyl)phenyl metaborate. Moreover, it is also possible to use a suitable combination of compounds which can produce such a boric acid ester in the reaction system.

The above-described carboxyl compounds and boric acid ester compounds, which are useful as additives, may be used alone or in admixture of two or more. These additives may usually be used in an amount of not greater than 50 moles, preferably about 0.001 to about 20 moles, per mole of the indole compound.

In the process of the present invention, no particular limitation is placed on the method by which the reaction is carried out. There may be employed any method that permits at least the indole compound, organic hydroperoxide and additive to be effectively mixed or contacted with each other, and the reaction may be carried out in any of batch, semibatch and continuous operations. More specifically, there may be employed a method in which the indole compound, organic hydroperoxide and additive are charged into a reactor all at once, a method in which one of the materials is continuously or intermittently added to a mixture of the other two, a method in which two of the materials are similarly added to the other, or a method in which the three materials are continuously or intermittently fed to a reactor.

The reaction temperature and the reaction time may vary according to the types and amounts of the indole compound, organic hydroperoxide and additive used. However, the reaction temperature is usually in the range of about −10° C. to about 200° C. If the reaction temperature is too low, the reaction will become unduly slow, while if it is too high, the reaction may be attended with danger because of violent decomposition of the organic hydroperoxide. Preferably, the reaction temperature is in the range of about 10° C. to about 150° C. The reaction time is usually within about 50 hours and preferably in the range of about 0.01 to about 20 hours. According to circumstances, the reaction may be carried out under reduced, atmospheric or superatmospheric pressure.

In the process of the present invention, the reaction may be carried out under an atmosphere of an inert gas or in the presence of molecular oxygen such as air.

In the process of the present invention, the yield of the indigo compound or the reaction rate can be enhanced by additionally using a metallic compound catalyst capable of oxidizing carbon atom at the 3-position of the indole compound. Accordingly, it is very preferable to use such a catalyst. The term "metallic compound catalyst capable of oxidizing carbon atom at the 3-position of the indole compound" comprehends compounds of metals which, in the reaction of the indole compound with the organic hydroperoxide, can cause carbon atom at the 3-position of the indole compound to be oxidized by an oxygen atom. For example, this catalyst is at least one compound selected from the group consisting of compounds of the metals of groups 4A, 5A and 6A of the periodic table. Specifically, useful metallic compounds include various compounds of titanium, zirconium, hafnium, vanadium, niobium, tantalum, chromium, molybdenum and tungsten. More specifically, they include inorganic compounds of the aforesaid metals, such as halides, oxyhalides, oxides, mixed oxides, sulfides, borides, phosphides, hydroxides, oxyhydroxides, cyano complexes, inorganic acid salts (e.g., sulfates, nitrates and phosphates), metallic oxyacids (e.g., titanic acid, molybdic acid and tungstic acid) and salts thereof, and heteropoly-acids (e.g., phosphomolybdic acid and silicotungstic acid) and salts thereof; compounds of the aforesaid metals having an organic group in at least a portion thereof, such as organic acid salts (e.g., acetates, oxalates, benzoates and naphthenates), alkoxides (e.g., those derived from ethyl alcohol and isopropyl alcohol), phenoxides (e.g., those derived from phenol and m-chlorophenol), and halogen compounds having an alkoxy or phenoxy group; complex compounds of the aforesaid metals, such as carbonyl complexes, amine complexes, pyridine complexes (e.g., those derived from pyridine and bipyridyl), oxo complexes, thiolate complexes (e.g., those derived from cysteine and dithiocatechol), sulfide complexes, dithiocarbamate complexes, thiocyanate complexes, isocyanate complexes, nitrosyl complexes, phosphine complexes (e.g., those derived from triphenylphosphine and 1,2-diphenylphosphinoethane), phosphoryl complexes, phthalocyanine complexes, porphyrin complexes, nitrile complexes, ether complexes, ketone complexes, $\beta$-ketocarbonyl complexes (e.g., those derived from acetylacetone), alkyl and allene complexes, olefin complexes and cyclopentadienyl complexes; and compounds of the aforesaid metals coming under two or more of the foregoing categories. These metallic compounds may be used alone or in admixture of two or more. It is also possible to use a suitable combination of components which can produce any of these metallic compounds in the reaction system. Although these metallic compounds are preferably soluble in the reaction mixture, they may be partially or totally insoluble therein. These metallic compounds are usually used in an amount of not greater than 0.5 mole, preferably 0.00001 to 0.1 mole, per mole of the indole compound.

Although the process of the present invention may be carried out in the absence of a solvent, it is usually carried out in the presence of a solvent. For this purpose, there may be used any solvent that does not interfere with the reaction. Useful solvents include, for example, water; aliphatic and alicyclic hydrocarbons such as n-hexane, n-pentane and cyclohexane; aromatic hydrocarbons such as benzene, toluene, ethylbenzene and cumene; aliphatic and aromatic halogen compounds such as dichloromethane, chloroform, chlorobenzene and dichlorobenzene; ethers such as diethyl ether, diphenyl ether, tetrahydrofuran and ethylene glycol diethyl ether; alcohols such as methanol, ethanol, tert-butanol cyclohexanol, benzyl alcohol and propylene glycol; ketones such as acetone, methyl ethyl ketone and acetophenone; esters such as ethyl acetate and ethyl propionate; carbonates such as dimethyl carbonate; and aromatic nitro compounds such as nitrobenzene. These solvents may be used alone or in admixture of two or more. When these solvents are used, it does not matter whether the reaction mixture forms a homogeneous system or a heterogeneous system consisting of a plurality of phases.

In the process of the present invention, the desired indigo compound can be obtained by working up the resulting reaction mixture in the usual manner. On completion of the reaction, most of the formed indigo compound has usually separated out. Therefore, the indigo compound can easily be recovered as a solid according to a conventional solid-liquid separation technique such as filtration, centrifugation or decantation. Where the amount of the precipitated indigo compound is insufficient, it is also possible to concentrate the reaction mixture and then recover the resulting increased amount of precipitate therefrom.

The present invention is further illustrated by the following examples. These examples are intended to illustrate the invention and are not to be construed to limit the scope of the invention.

EXAMPLE 1

A three neck flask having a capacity of 100 ml and fitted with a stirrer, a thermometer and a cooling coil was charged with 1.0 g (8.5 mmoles) of indole, 104.2 mg (0.85 mmole) of benzoic acid as an additive, 30 g of toluene as a solvent, and 7.83 g (42.7 mmoles as cumene hydroperoxide) of an 83 wt. % solution of cumene hydroperoxide in cumene (hereinafter referred to briefly as the CHP solution), all at once. This reaction mixture was heated at 80° C. on an oil bath and stirred under an atmosphere of air for 10 hours to effect the reaction. The reaction mixture was homogeneous at the start of the reaction, but a deep blue solid gradually precipitated out with the progress of the reaction. After completion of the reaction, this reaction mixture was filtered. The solid so separated was washed with a small amount of toluene and then dried at 50° C. under reduced pressure to obtain 108.6 mg of a deep blue solid product. Elemental analysis and IR spectroscopic analysis revealed that this product was indigo. The molar yield of the isolated indigo as based on the charged indole (hereinafter referred to briefly as the indigo yield) was 9.7% and the indigo yield per hour, which serves as a measure of its formation rate, was 1.0%.

COMPARATIVE EXAMPLE 1

Reaction and after-treatment were carried out in the same manner as in Example 1, except that the use of benzoic acid was omitted. Thus, there was obtained 24.5 mg of indigo. The indigo yield was 2.2% and the indigo yield per hour was 0.2%. The omission of the additive resulted in a low yield and a slow formation rate.

EXAMPLES 2–5

Reaction and after-treatment were carried out in the same manner as in Example 1, except that the type and amount of additive used, the type and amount of solvent used, the reaction temperature and the reaction time were altered as shown in Table 1. The results thus obtained, together with those of Examples 1 and Comparative Example 1, are shown in Table 1. All of these examples gave improved results in yield and formation rate as compared with the results obtained with no additive.

EXAMPLE 6

A three neck flask having a capacity of 500 ml and fitted with a stirrer, a thermometer and a cooling coil was charged with 10.0 g (85.4 mmoles) of indole, 1.04 g (8.5 mmoles) of benzoic acid as an additive, 225 mg (0.85 mmole) of molybdenum hexacarbonyl as a catalyst, 300 g of cumene as a solvent, and 47.0 g (256.3 mmoles as cumene hydroperoxide) of the CHP solution, all at once. This reaction mixture was heated at 80° C. on an oil bath and stirred under an atmosphere of air for 5 hours to effect the reaction. After completion of the reaction, this reaction mixture was filtered. The solid so separated was washed with small amounts of cumene and methanol, and then dried at 50° C. under reduced pressure to obtain 7.91 g of indigo. The indigo yield was 70.7% and the indigo yield per hour was 14.1%.

COMPARATIVE EXAMPLE 2

Reaction and after-treatment were carried out in the same manner as in Example 6, except that the use of benzoic acid was omitted. Thus, there was obtained 5.91 g of indigo. The indigo yield was 52.8% and the indigo yield per hour was 10.6%. Similarly to Comparative Example 1, the omission of the additive resulted in a low yield and a slow formation rate.

EXAMPLES 7–30

Reaction and after-treatment were carried out in the same manner as in Example 6, except that the benzoic acid was replaced by each of the additives whose type and amount are shown in Table 2. The results thus obtained, together with those of Examples 6 and Comparative Example 2, are shown in Table 2. In all of these examples, the results show an improvement in yield and formation rate as compared with the results of Comparative Example 2 using no additive.

EXAMPLES 31–38

Reaction and after-treatment were carried out in the same manner as in Example 1, except that the amounts of indole and the CHP solution used, the types and amounts of additive and solvent used, the reaction temperature and the reaction time were altered as shown in Table 3, and that each of the catalysts listed in Table 3 was used in the indicated amount. The results thus obtained are shown in Table 3.

COMPARATIVE EXAMPLES 3–10

The procedures of Examples 31–38 were repeated except that the additive used in each of the examples was omitted. The results thus obtained, together with those of Examples 33–40, are shown in Table 3. In all of these comparative examples, the omission of the additive resulted in a low yield and a slow formation rate.

EXAMPLE 39

Reaction was carried out in the same manner as in Example 1, except that 87.1 mg (0.85 mmole) of acetic anhydride was used in the place of benzoic acid, 22.5 mg (0.085 mmole) of molybdenum hexacarbonyl was additionally used as a catalyst, and the reaction time was altered to 5 hours. After completion of the reaction, the reaction mixture was filtered. The solid so separated was washed with a small amount of toluene, and then washed with water and methanol, and dried at 50° C. under reduced pressure. As a result, the indigo yield was 61.7% and the indigo yield per hour was 12.3%.

COMPARATIVE EXAMPLE 11

Reaction and after-treatment were carried out in the same manner as in Example 39, except that the use of lithium acetate dihydrate was omitted. As a result, the indigo yield was 50.9% and the indigo yield per hour was 10.2%.

EXAMPLE 40

A four neck flask having a capacity of 100 ml and fitted with a stirrer, a thermometer, a dropping funnel and a cooling coil was charged with 1.0 g (8.5 mmoles) of indole, 104.2 mg (0.85 mmole) of benzoic acid as an additive, 11.3 mg (0.043 mmole) of molybdenum hexacarbonyl as a catalyst, and 30 g of toluene as a solvent. While this mixture was being heated at 80° C. on an oil bath and stirred under an atmosphere of air, 5.6 g (42.9 mmoles as tert-butyl hydroperoxide) of a 69 wt. % aqueous solution of tert-butyl hydroperoxide was added dropwise thereto over a period of one hour. Thereafter, the reaction was continued for 5 hours under the same conditions. The resulting reaction mixture was worked up in the same manner as in Example 1. As a result, the indigo yield was 29.3% and the indigo yield per hour was 5.9%.

EXAMPLES 41–43

Reaction and after-treatment were carried out in the same manner as in Example 40, except that the amounts of indole and benzoic acid used were altered as shown in Table 4 and the 69 wt. % aqueous solution of tert-butyl hydroperoxide was replaced by each of the organic hydroperoxides whose type and amount are shown in Table 4. The results thus obtained, together with those of Examples 52, are shown in Table 4. All of these examples gave improved results in yield and formation rate as compared with the results obtained with no additive.

EXAMPLE 44

Reaction was carried out in the same manner as in Example 1, except that 3.0 g (19.8 mmoles) of 5-chloroindole was used in place of the indole, the CHP solution was used in an amount of 18.0 g (98.2 mmoles as cumene hydroperoxide), 309.8 mg (1.98 mmoles) of p-chlorobenzoic acid was used in place of the benzoic acid, 22.5 mg (0.085 mmole) of molybdenum hexacarbonyl was additionally used as a catalyst, and the reaction time was altered to 5 hours. The resulting reaction mixture was filtered. The solid so separated was washed with a small amount of methanol and then dried at 50° C. under reduced pressure to obtain 1.64 g of the corresponding indigo compound, or 5,5'-dichloroindigo. The molar yield of 5,5'-dichloroindigo as based on the charged 5-chloroindole was 50.1%.

EXAMPLE 45

Reaction was carried out in the same manner as in Example 1, except that 1.0 g (7.6 mmoles) of 6-methylindole was used in place of the indole, the CHP solution was used in an amount of 7.0 g (38.2 mmoles as cumene hydroperoxide), 103.8 mg (0.76 mmole) of m-methylbenzoic acid was used in place of the benzoic acid, 22.5 mg (0.085 mmole) of molybdenum hexacarbonyl was additionally used as a catalyst, and the reaction time was altered to 5 hours. The resulting reaction mixture was filtered. The solid so separated was washed with a small amount of methanol and then dried at 50° C. under reduced pressure to obtain 0.64 g of the corresponding indigo compound, or 6,6'-dimethylindigo. The molar yield of 6,6'-dimethylindigo as based on the charged 6-methylindole was 57.8%.

TABLE 1

| Example No. | Additive Type | Additive Amount used | Solvent Type | Solvent Amount used (g) | Temperature (°C.) | Time (hr) | Indigo yield (%) | Indigo yield per hour (%) |
|---|---|---|---|---|---|---|---|---|
| Example 1 | Benzoic acid | 104.2 mg | Toluene | 30 | 80 | 10 | 9.7 | 1.0 |
| Comparative Example 1 | None | | Toluene | 30 | 80 | 10 | 2.2 | 0.2 |
| Example 2 | Acetic acid | 51.0 mg | Cumene | 20 | 90 | 10 | 8.3 | 0.8 |
| Example 3 | Acetic anhydride | 87.1 mg | Toluene | 50 | 70 | 5 | 12.6 | 2.5 |
| Example 4 | Cyclohexyl metaborate | 3.21 g | Toluene | 30 | 80 | 5 | 23.2 | 4.6 |
| Example 5 | Triisopropyl borate | 4.82 g | Cumene | 30 | 90 | 10 | 10.1 | 1.0 |

TABLE 2

| Example No. | Additive Type | Amount used (g) | Indigo yield (%) | Indigo yield per hour (%) |
|---|---|---|---|---|
| Example 6 | Benzoic acid | 1.04 | 70.7 | 14.1 |
| Example 7 | o-Chlorobenzoic acid | 1.34 | 65.9 | 13.2 |
| Example 8 | m-Chlorobenzoic acid | 0.67 | 72.5 | 14.5 |
| Example 9 | p-Chlorobenzoic acid | 1.34 | 72.7 | 14.6 |
| Example 10 | p-Bromobenzoic acid | 1.72 | 72.0 | 14.4 |
| Example 11 | m-Hydroxybenzoic acid | 1.18 | 71.2 | 14.2 |
| Example 12 | p-Hydroxybenzoic acid | 1.77 | 70.5 | 14.1 |
| Example 13 | m-Methoxybenzoic acid | 2.60 | 69.1 | 13.8 |
| Example 14 | p-Methoxybenzoic acid | 1.30 | 66.7 | 13.3 |
| Example 15 | α-Naphthalenecarboxylic acid | 2.94 | 68.7 | 13.7 |
| Example 16 | Terephthalic acid | 0.71 | 55.5 | 11.1 |
| Example 17 | Isophthalic acid | 1.42 | 63.5 | 12.7 |
| Example 18 | Acetic acid | 0.51 | 65.5 | 13.1 |
| Example 19 | Propionic acid | 0.63 | 67.0 | 13.4 |
| Example 20 | Octanoic acid | 1.23 | 66.7 | 13.3 |
| Example 21 | Phenylacetic acid | 2.32 | 70.5 | 14.1 |
| Example 22 | Diphenylacetic acid | 3.62 | 71.4 | 14.3 |
| Example 23 | Pivalic acid | 0.87 | 65.6 | 13.1 |
| Example 24 | Cyclohexanecarboxylic acid | 1.09 | 69.2 | 13.8 |
| Example 25 | Cinnamic acid | 1.26 | 63.7 | 12.7 |
| Example 26 | Succinic acid | 0.50 | 60.8 | 12.2 |
| Example 27 | Fumaric acid | 0.99 | 65.3 | 13.1 |
| Example 28 | Naphthenic acid | 1.00 | 64.8 | 13.0 |
| Example 29 | Isonicotinic acid | 1.05 | 63.2 | 12.6 |
| Example 30 | Nicotinic acid | 0.53 | 57.5 | 11.5 |
| Comparative Example 2 | None | | 52.8 | 10.6 |

TABLE 3

| Example No. | Indole Amount used (g) | CHP solution Amount used (g) | Additive Type | Additive Amount used (mg) | Catalyst Type | Catalyst Amount used (mg) |
|---|---|---|---|---|---|---|
| Example 31 | 1.0 | 4.68 | p-Methylbenzoic acid | 58 | Mo(CO)$_6$ | 2.3 |
| Comparative Example 3 | 1.0 | 4.68 | None | | Mo(CO)$_6$ | 2.3 |
| Example 32 | 1.0 | 4.68 | Acetic acid | 51 | MoCl$_5$ | 23.2 |
| Comparative Example 4 | 1.0 | 4.68 | None | | MoCl$_5$ | 23.2 |
| Example 33 | 1.0 | 7.83 | m-Chlorobenzoic acid | 134 | MoO$_3$ | 12.2 |
| Comparative Example 5 | 1.0 | 7.83 | None | | MoO$_3$ | 12.2 |
| Example 34 | 1.0 | 7.83 | Propionic acid | 63 | MoS$_2$ | 136.1 |
| Comparative Example 6 | 1.0 | 7.83 | None | | MoS$_2$ | 136.1 |
| Example 35 | 1.0 | 4.68 | Benzoic acid | 208 | [Mo(OOCPh)$_2$]$_2$ | 3.1 |
| Comparative Example 7 | 1.0 | 4.68 | None | | [Mo(OOCPh)$_2$]$_2$ | 3.1 |
| Example 36 | 1.0 | 4.68 | Benzoic acid | 104 | MoO$_2$(cys-OMe)$_2$ | 3.4 |
| Comparative Example 8 | 1.0 | 4.68 | None | | MoO$_2$(cys-OMe)$_2$ | 3.4 |
| Example 37 | 1.0 | 7.83 | p-Hydroxybenzoic acid | 118 | Ti(OiPr)$_4$ | 24.2 |
| Comparative Example 9 | 1.0 | 7.83 | None | | Ti(OiPr)$_4$ | 24.2 |
| Example 38 | 5.0 | 23.5 | Cinnamic acid | 365 | W(CO)$_6$ | 299.1 |

TABLE 3-continued

| | | | Solvent | | | | Indigo yield |
|---|---|---|---|---|---|---|---|
| Example No. | | Type | Amount used (g) | Temperature (°C.) | Time (hr) | Indigo yield (%) | per hour (%) |
| Comparative Example 10 | 5.0 | 23.5 | None | W(CO)$_6$ | | | 299.1 |
| Comparative Example 11 | | | None | | | | |
| Example 31 | | DPO | 30 | 100 | 5 | 62.3 | 12.5 |
| Comparative Example 3 | | DPO | 30 | 100 | 5 | 51.9 | 10.4 |
| Example 32 | | Methylene chloride | 50 | 20 | 10 | 13.5 | 1.4 |
| Comparative Example 4 | | Methylene chloride | 50 | 20 | 10 | 9.2 | 0.9 |
| Example 33 | | ODCB | 20 | 100 | 2 | 29.1 | 14.6 |
| Comparative Example 5 | | ODCB | 20 | 100 | 2 | 23.7 | 11.9 |
| Example 34 | | Nitrobenzene | 30 | 80 | 5 | 24.9 | 5.0 |
| Comparative Example 6 | | Nitrobenzene | 30 | 80 | 5 | 19.4 | 3.9 |
| Example 35 | | Cumene | 30 | 100 | 5 | 57.7 | 11.5 |
| Comparative Example 7 | | Cumene | 30 | 100 | 5 | 30.8 | 6.2 |
| Example 36 | | CHBz | 30 | 100 | 5 | 48.3 | 9.7 |
| Comparative Example 8 | | CHBz | 30 | 100 | 5 | 38.0 | 7.6 |
| Example 37 | | Toluene | 30 | 80 | 5 | 20.2 | 4.0 |
| Comparative Example 9 | | Toluene | 30 | 80 | 5 | 14.8 | 3.0 |
| Example 38 | | Toluene | 30 | 80 | 5 | 18.8 | 3.8 |
| Comparative Example 10 | | Toluene | 30 | 80 | 5 | 15.1 | 3.0 |
| Comparative Example 11 | | | | | | 50.9 | 10.2 |

Note:
"OOCPh", "cys-OMe" and "OiPr" represent a benzoate group, a methyl L-cystenate group and an isopropoxy group, respectively. "DPO", "ODCB" and "CHBz" represent diphenyl ether, o-dichloro-benzene and cyclohexylbenzene, respectively. "CHP solution" represents an 83 wt. % solution of cumene hydroperoxide in cumene.

TABLE 4

| Example No. | Indole Amount used (g) | Benzoic acid Amount used (mg) | Organic hydroperoxide Type | Amount used (g) | Indigo yield (%) | Indigo yield per hour (%) |
|---|---|---|---|---|---|---|
| Example 40 | 1.0 | 104 | 69 wt. % aqueous solution of tert-butyl hydroperoxide | 5.6 | 40.1 | 8.0 |
| Example 41 | 1.0 | 52 | 54 wt. % solution of bis(1-methylethyl)phenyl hydroperoxide in diisopropylbenzene | 9.2 | 59.4 | 11.9 |
| Example 42 | 5.0 | 520 | 53 wt. % solution of 1-methyl-1-(4-methylcyclohexyl)ethyl hydroperoxide in p-menthane | 41.3 | 57.3 | 11.5 |
| Example 43 | 1.0 | 208 | 90 wt. % solution of 1,1,3,3-tetramethylbutyl hydroperoxide in 1,1,3,3-tetramethylbutane | 4.2 | 61.1 | 12.2 |

We claim:

1. In a method for the preparation of an indigo compound wherein an indole compound is oxidized, the improvement wherein the starting indole lacks a substituent at the 2- and 3- positions and is oxidized in one step to the indigo compound with an organic hydroperoxide in the presence of an additive selected from the group consisting of (1) a carboxyl compound and (2) a boric acid ester compound.

2. A process as claimed in claim 1 wherein the indole compound having no substituent at the 2- and 3-positions is indole.

3. A process as claimed in claim 1 wherein the organic hydroperoxide is a compound selected from the group consisting of secondary and tertiary alkyl hydroperoxides.

4. A process as claimed in claim 1 wherein the organic hydroperoxide is tert-butyl hydroperoxide, 1-phenylethyl hydroperoxide or 1-methyl-1-phenylethyl hydroperoxide.

5. A process as claimed in claim 1 wherein the organic hydroperoxide is used in an amount of 0.01 to 100 moles per mole of the indole compound.

6. A process as claimed in claim 1 wherein the carboxyl compound is a compound selected from the group consisting of carboxylic acids and carboxylic acid anhydrides.

7. A process as claimed in claim 1 wherein the boric acid ester compound is a compound selected from the group consisting of orthoboric acid esters and metaboric acid esters.

8. A process as claimed in claim 1 wherein the additive selected from the group consisting of a carboxyl compound and a boric acid ester compound is used in an amount of not greater than 50 moles per mole of the indole compound.

9. A process as claimed in claim 1 wherein the indole compound having no substituent at the 2- and 3- positions is indole, wherein the organic hydroperoxide is tert-butyl hydroperoxide, 1-phenylethyl hydroperoxide or 1-methyl-1-phenylethyl hydroperoxide, and wherein the reaction temperature is in the range of $-10°$ to $200°$ C.

10. A process as claimed in claim 1 wherein the reaction is carried out in the presence of at least one solvent selected from the group consisting of water, aliphatic and alicyclic hydrocarbons, aromatic hydrocarbons, aliphatic and aromatic halogen compounds, ethers, alcohols, ketones, esters, carbonates and aromatic nitro compounds.

11. A process as claimed in claim 1 wherein the formed indigo compound is recovered in the form of a solid according to a solid-liquid separation technique.

12. A process as claimed in claim 1 wherein the reaction is carried out in the presence of a metallic compound catalyst capable of oxidizing the carbon atom at the 3-position of the indole compound.

13. A process as claimed in claim 12 wherein the metallic compound catalyst is a compound of a metal selected from the group consisting of groups 4A, 5A and 6A of the periodic table.

14. A process as claimed in claim 12 wherein the metallic compound catalyst is a compound selected from the group consisting of compounds of titanium, vanadium, molybdenum and tungsten.

15. A process as claimed in claim 12 wherein the metallic compound catalyst is a compound of molybdenum.

16. A process as claimed in claim 12 wherein the metallic compound catalyst is used in an amount of not greater than 0.5 mole per mole of the indole compound.

17. A process as claimed in claim 12 wherein the indole compound having no substituent at the 2- and 3-positions is indole.

18. A process as claimed in claim 12 wherein the organic hydroperoxide is a compound selected from the group consisting of secondary and tertiary alkyl hydroperoxides.

19. A process as claimed in claim 12 wherein the organic hydroperoxide is tert-butyl hydroperoxide, 1-phenylethyl hydroperoxide or 1-methyl-1-phenylethyl hydroperoxide.

20. A process as claimed in claim 12 wherein the organic hydroperoxide is used in an amount of 0.01 to 100 moles per mole of the indole compound.

21. A process as claimed in claim 12 wherein the carboxyl compound is a compound selected from the group consisting of carboxylic acids and carboxylic acid anhydrides.

22. A process as claimed in claim 12 wherein the boric acid ester compound is a compound selected from the group consisting of orthoboric acid esters and metaboric acid esters.

23. A process as claimed in claim 12 wherein the additive selected from the group consisting of a carboxyl compound and a boric acid ester compound is used in an amount of not greater than 50 moles per mole of the indole compound.

24. A process as claimed in claim 12 wherein the indole compound having no substituent at the 2- and 3-positions is indole, wherein the organic hydroperoxide is tert-butyl hydroperoxide, 1-phenylethyl hydroperoxide or 1-methyl-1-phenylethyl hydroperoxide, and wherein the reaction temperature is in the range of $-10°$ to $200°$ C.

25. A process as claimed in claim 12 wherein the reaction is carried out in the presence of at least one solvent selected from the group consisting of water, aliphatic and alicyclic hydrocarbons, aromatic hydrocarbons, aliphatic and aromatic halogen compounds, ethers, alcohols, ketones, esters, carbonates and aromatic nitro compounds.

26. A process as claimed in claim 12 wherein the formed indigo compound is recovered in the form of a solid according to a solid-liquid separation technique.

* * * * *